United States Patent [19]

Moudry et al.

[11] 3,991,047
[45] Nov. 9, 1976

[54] PROCESS FOR PREPARING LACTAMS

[75] Inventors: Radomir Moudry, Domat, Bruno Domeisen; Hanswerner Philipp, both of Chur, all of Switzerland

[73] Assignee: Inventa AG fur Forschung und Patentverwertung, Zurich, Switzerland

[22] Filed: Aug. 27, 1975

[21] Appl. No.: 608,249

[30] Foreign Application Priority Data

Sept. 3, 1974 Switzerland............... 011926/74

[52] U.S. Cl................. 260/239.3 A; 423/356; 423/357; 423/541 A; 423/542
[51] Int. Cl.²............................. C07D 201/16
[58] Field of Search......... 260/239.3 A; 423/356, 423/357, 541, 542

[56] References Cited
UNITED STATES PATENTS

| | | | |
|---|---|---|---|
| 2,182,078 | 12/1939 | Fleming et al. | 423/357 |
| 2,221,369 | 11/1940 | Cass | 260/239.3 A |
| 2,313,026 | 3/1943 | Schlack | 260/239.3 A |
| 2,687,946 | 8/1954 | Manning et al. | 423/541 |
| 2,687,947 | 8/1954 | Manning et al. | 423/541 |
| 2,781,245 | 2/1957 | Robertson et al. | 423/357 |
| 3,282,646 | 11/1966 | Bonfield et al. | 423/541 A |
| 3,852,272 | 12/1974 | De Rooij et al. | 260/239.3 A |
| 3,852,273 | 12/1974 | De Rooij et al. | 260/239.3 A |
| 3,865,602 | 2/1975 | Stich et al. | 423/541 |

*Primary Examiner*—Natalie Trousof
*Assistant Examiner*—Robert T. Bond
*Attorney, Agent, or Firm*—Bierman & Bierman

[57] ABSTRACT

In a process for the preparation of lactam from cycloalkanone comprising reacting said alkanone with hydroxylamine sulfate to form the corresponding cycloalkanone oxime followed by Beckman rearrangement to yield said lactam and neutralization of the sulfuric acid formed by ammonia whereby ammonium sulfate is formed as a byproduct, the improvement which comprises reacting said ammonium sulfate with an alkaline-earth metal oxide or hydroxide to form an alkaline earth metal sulfate and ammonia, heating said alkaline-earth metal sulfate to decompose it into said alkaline-earth metal oxide and sulfur dioxide and/or sulfur trioxide, converting said sulfur dioxide and/or sulfur trioxide into sulfuric acid, whereby said sulfuric acid and said ammonia are capable of reuse in said process.

8 Claims, No Drawings

PROCESS FOR PREPARING LACTAMS

This invention is an improvement on an existing process for the preparation of lactams from cycloalkanones. It has been known, in the past, to prepare lactams from cycloalkanones by reacting hydroxylamine sulfate with the alkanone to form the corresponding oxime. In this reaction sulfuric acid is liberated and this acid is neutralized with ammonia to produce ammonium sulfate as a byproduct. The oxime is converted to the desired lactam by the Beckmann rearrangement by using sulfuric acid followed by neutralization of the rearrangement mixture with ammonia. The desired lactam is then separated from the ammonium sulfate formed.

As can be seen from the foregoing, a yield of ammonium sulfate is entailed in this process which amounts to approximately 1 to 4 tons per ton of lactam. The ammonium sulfate obtained may be processed into crystalline ammonium sulfate which is useful as a fertilizer. Sometimes purification is desirable, but this is not always necessary.

In recent years, however, the need for ammonium sulfate has diminished and, therefore, a need has arisen for a lactam synthesis which produces little or no ammonium sulfate. This is particularly true as regards the preparation of caprolactam and dodecalactam. These two lactams are quite important commercially and they can each be produced separately, or they can be jointly produced by colactamization. The process of the present invention can be applied to such syntheses and also to any process showing an undesirable yield of ammonium sulfate.

In one prior art process, an attempt has been made to decompose the ammonium sulfate and to employ the decomposition products in the basic lactam synthesis. In this process, ammonia is split off from the ammonium sulfate by heating, thus forming ammonium hydrogen sulfate. This ammonia is the n used for neutralization of either the oxime-formation mixutre or the rearrangement mixture or both. The sulfate melt formed on the splittng off of the ammonia is burned to form a gas containing sulfur dioxide, which is then converted to sulfuric acid or oleum in the usual known manner. The sulfuric acid is then returned to the lactam synthesis.

This process has a number of important disadvantages. Only half of the ammonia can be recovered and the second half burned in the recovery of sulfur dioxide to form nitrogen and water. In actuality, even this yield is not achieved. When the ammonium sulfate is split to yield one of its two molecules of ammonia, some of the ammonia is already partially oxidized to yield nitrogen and water. In addition, sulfur dioxide is also formed during this step. As a result, the yield of ammonia, as well as the yield of sulfur dioxide, is directly dependent upon the temperature. Thus, the ammonia which is split off from the ammonium sulfate is always contaminated with sulfur dioxide. This not only reduces the yield of sulfur dioxide, but also introduces purification problems.

By the process of the present invention, it is possible to produce lactams by the aforementioned Beckmann rearrangement while, at the same time, breaking down the ammonium sulfate produced into products which can be reused in the synthesis. Thus, all byproducts obtained by the process of the present invention can be further employed within the process itself and recycled substantially without losses.

In the present process, the ammonium sulfate produced both during the oxime formation and the rearrangement steps is reacted with an alkaline-earth metal oxide or hydroxide. This forms the corresponding alkaline-earth metal sulfate and liberates ammonia. The ammonia is then employed to neutralize the rearrangement and/or oxime-formation mixtures.

The alkaline-earth metal sulfate is decomposed by heat to yield the alkaline-earth metal oxide and sulfur dioxide. It is preferable to use a reducing agent during this step. By so doing, the temperature required for decomposing the metal sulfate is substantially reduced. The sulfur dioxide is converted to sulfuric acid or oleum which is used in the lactam synthesis. Similarly, the alkaline-earth metal oxide is used to liberate ammonia from the ammonium sulfate solution obtained in this same synthesis. Thus, it can be seen that all of the byproducts are broken down and reused in the same process so that there is no excess ammonium sulfate produced.

This process can be illustrated by the following reaction (wherein Me represents alkaline-earth metal):

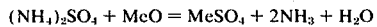

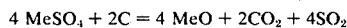

The foregoing process has numerous advantages when compared with existing methods of decomposing ammonium sulfate. In particular, the splitting off of ammonia takes place at a reduced temperature, so that no sulfur dioxide is split off during this step and therefore, no additional purification of the liberated ammonia need be carried out. In addition, there is no ammonium sulfate present on the recovery of the sulfur dioxide, and therefore there is no danger of the formation of undesired and dangerous nitric oxides.

The hydroxyl amine sulfate used in the lactam synthesis may contain a small amount of ammonium sulfate. This is formed as a result of the undesired reduction of nitric oxide to ammonia. In the present process, this impurity is treated in the normal manner and presents no problem whatsoever. In addition, the impurity actually provides a benefit in that some additional ammonia is produced which will serve to cover any losses encountered during the carrying out of this process. Thus, what has heretofore been considered an undesirable impurity has been coverted into a positive asset.

As an alternative, the decomposition of the sulfate may be carried out imcompletely, and the remaining sulfate is then recycled with the alkaline-earth metal oxide.

It has been found of particular advantage to covert the alkaline-earth metal oxide into the corresponding hydroxide (in known manner) before reaction with ammonium sulfate. This modification of the present process accelerates the liberation of ammonia from the sulfate.

The process for preparing lactams by Beckmann rearrangement of cycloalkanone oximes produced from cycloalkanones by reaction with hydroxylamine sulfate solution is accordingly characterized in that ammonia is liberated from the ammonium sulfate obtained in the course of the process by treatment with alkaline-earth metal oxide to form the corresponding alkaline-earth metal sulfate. The alkaline-earth metal sulfate obtained is decomposed into alkaline-earth metal oxide and sulfur dioxide or sulfur trioxide by thermal treatment (with the addition of a reducing agent if necessary), and the sulfur oxides are converted into sulfuric acid or oleum. The quantitatively recovered constituents of the ammonium sulfate; namely, ammonia and sulfuric acid or oleum, are reused for lactam preparation, and the alkaline-earth metal oxide obtained in the course of the process is employed again for liberating ammonia.

Of course, if calcium oxide/hydroxide is used, the calcium sulfate produced during the decomposition of the ammonium sulfate is useful as such in the plaster industry. The $SO_2$ obtained can be worked up once more into sulfuric acid and returned to the lactam synthesis.

In the process according to the invention the use of reducing agents is preferred. In this connection, carbon is particularly suitable, especially in the form of charcoal, whereby the operating temperatures can be lowered by some hundreds of degrees.

Example 1 a. 9.8 g of cyclohexanone were added to a hydroxylamine sulfate solution (resulting from NO reduction) of the following composition: 8.2 g hydroxylamine sulfate, 2.2 g sulfuric acid, 0.8 g ammonium sulfate and 32.0 g water. The mixture was neutralized to pH 4.1 by stirring with concentrated ammonia solution. 2.50 of 100% ammonia were consumed. The oxime was then extracted five times with 40 ml of benzene, the benzene extracts were combined, concentrated by evaporation and rearranged with 15.0 g of oleum (20.0% free $SO_3$) in known manner to give caprolactam. The mixture was diluted with water and neutralized to pH 4 with concentrated ammonia solution (the consumption of 100% ammonia was 5.45 g) and extracted five times with 40 ml of benzene. The combined and concentrated benzene extracts yielded 10.4 g of crude caprolactam (melting point 67.5° C), which constituted 92% of the theoretical. The aqueous layers obtained during the oxime-formation and rearrangement were combined. The amount thereof was 98.0 g.

b. 3.90 g of calcium hydroxide were added to one fifth (19.6 g) of the aqueous solution of Example 1a and the mixture was agitated by blowing air through it. The ammonia liberated in the process was passed through prepared sulfuric acid solution. After one hour, the temperature of the reaction flask was increased, so that the water also distilled at the same time and, after about 30 minutes, a solid residue was left. By back titration of the prepared sulfuric acid, 1.58 g of ammonia were found, which equaled 97% of the ammonia present and 99.5% of the ammonia employed for neutralization in the oxime-formation and rearrangement.

The residue left after the removal of the ammonia was mixed with 0.35 g of charcoal and placed in a titanium boat enclosed in a tube furnace which was connected to an air inlet tube and a product outlet tube. The temperature of the mixture was raised to 1180° C within 90 minutes and held at this temperature for 80 minutes. The product gases were collected in water which was in cascades connected to the outlet tube. Analysis of this water showed that it contained 0.0468 gmol of the sulfur oxides, equaling 97.8% of the sulfur trioxide present. The residue in the titanium boat weighed 2.94 g, which almost exactly corresponded to the theoretical amount of calcium oxide.

c. 3.10 g of calcium oxide were added to one fifth (19.60 g) of the aqueous solution of Example 1a and the mixture was treated just as in Example 1b, with the sole difference that the blowing-through of air lasted for two hours. 1.60 g of ammonia were found, which signified 98.5% of the ammonia present and 101.0% of the ammonia employed for neutralization in the oxime-formation and rearrangement. The residue left after the removal of the ammonia was treated as in Example 1b and 97.6% of the sulfur trioxide present was found in the cascades. The residue in the titanium boat weighed 3.08 g.

Example 2 a. A mixture of 5.9 g of cyclohexanone and 7.3 g of cyclododecanone was added dropwise while stirring to a hydroxylamine sulfate solution (resulting from NO reduction) of the following composition: 8.2 g hydroxylamine sulfate, 2.5 g sulfuric acid, 0.6 g ammonium sulfate and 35.4 g water, which was heated to 70° C, and the mixture was neutralized at the same time with concentrated ammonia solution to pH4. The ammonia consumption was 2.58 g (calculated as 100% ammonia). The oximes were then extracted 5 times with 40 ml of benzene, the benzene extracts were combined, concentrated by evaporation and rearranged with 17 g of oleum (19.2% free $SO_3$) in known manner to give lactams. The mixture was then diluted with water and neutralized to pH 4 with concentrated ammonia solution (the consumption of 100% ammonia was 6.15 g) and extracted five times with 40 ml of benzene. The combined and concentrated benzene extracts yielded 13.1 g of a mixture of crude caprolactam and laurinlactam. The aqueous layers obtained during the oxime formation and rearrangement were combined. The amount thereof was 102.5 g.

b. 2.30 g of magnesium oxide were added to one fifth (20.5 g) of the aqueous solution of Example 2a and the mixture was stirred by blowing air through it. The ammonia liberated in the process was passed through a prepared sulfuric acid solution. After 2 hours, the reaction flask was heated, so that the water also distilled at the same time and, after about 30 minutes, a solid residue was left. By back titration of the prepared sulfuric acid, 1.75 g of ammonia were found, which equaled 98.7% of the ammonia present and 100.2% of the ammonia employed for neutralization.

The residue left after the removal of the ammonia was placed in a titanium boat which was enclosed in a tube furnace as in Example 1b. The charge was heated to 1100° C within 90 minutes and held at that temperature for 120 minutes. The product gases contained 0.047 gmol of the sulfur dioxides, which equaled 93.5% of the sulfur trioxide present. The residue in the titanium boat weighed 2.57 g and still contained 6.53% of the undecomposed magnesium sulfate.

c. One fifth (20.5 g) of the aqeous solution of Example 2a was treated just as in Example 2b. 1.72 g of ammonia were found in the prepared sulfuric acid, equaling 97.0% of the ammonia present and 98.5% of the ammonia employed for neutralization in the oxime-formation and rearrangement.

The residue left after the removal of the ammonia was mixed with 0.9 g of charcoal and placed in a titanium boat enclosed in a tube furnace as in Example 1b. The charged mixture was heated to 800° C within 70 minutes and held at this temperature for 110 minutes. The product gases contained 0.051 gmol of the sulfur oxides, equaling 98.1% of the sulfur trioxide present. The residue in the titanium boat weighed 2.29 g.

What is claimed is:

1. In a process for the preparation of lactam from cycloalkanone comprising reacting said alkanone with hydroxylamine sulfate to form the corresponding cycloalkanone oxime followed by Beckmann rearrangement to yield said lactam and neutralization of the sulfuric acid formed and used by ammonia whereby ammonium sulfate is formed as a byproduct, the improvement which comprises reacting said ammonium sulfate with an alkaline-earth metal oxide to form an alkaline-earth metal sulfate and ammonia, heating said alkaline-earth metal sulfate to decompose it into said alkaline-earth metal oxide and sulfur dioxide and/or sulfur trioxide, converting said sulfur dioxide and/or sulfur trioxide into sulfuric acid, whereby said sulfuric acid and said ammonia are capable of reuse in said process.

2. A process according to claim 1 wherein a reducing agent is present during said heating.

3. A process according to claim 2 wherein said reducing agent is carbon.

4. A process according to claim 1 wherein said oxide is calcium or magnesium.

5. A process according to claim 1 wherein said oxide is converted to a hydroxide before said reaction with said ammonium sulfate.

6. A process according to claim 1 wherein said sulfur dioxide and/or sulfur trioxide is converted into sulfuric acid by addition of water.

7. A process according to claim 1 wherein said oxide is calcium oxide and at least a part of the calcium sulfate produced in the decomposition of ammonium sulfate is removed from said process.

8. A process accordng to claim 1, wherein said sulfuric acid and said ammonia are recycled and substantially no source of sulfuric acid or ammonia is added.

* * * * *